United States Patent [19]
McKenzie

[11] Patent Number: 5,955,286
[45] Date of Patent: Sep. 21, 1999

[54] METHOD FOR SCREENING COMPOUNDS FOR ACTIVITIES RELATED TO INSULIN RECEPTOR BINDING

[75] Inventor: Maureen A. McKenzie, Far Hills, N.J.

[73] Assignee: The State University of New Jersey, Piscataway, N.J.

[21] Appl. No.: 08/898,651

[22] Filed: Jul. 22, 1997

Related U.S. Application Data

[60] Continuation of application No. 08/361,232, Dec. 21, 1994, abandoned, which is a division of application No. 07/956,290, Oct. 5, 1992, Pat. No. 5,401,830.

[51] Int. Cl.⁶ .................................................. G01N 33/53
[52] U.S. Cl. ......................... 435/7.1; 435/7.31; 435/7.8; 435/194; 530/371; 530/303; 530/305; 530/350; 530/395; 530/824
[58] Field of Search ...................................... 435/7.1, 7.31, 435/7.8, 194; 530/371, 824, 303, 305, 350, 395

[56] References Cited

U.S. PATENT DOCUMENTS

| | | |
|---|---|---|
| 4,710,469 | 12/1987 | Liang et al. . |
| 4,774,321 | 9/1988 | Rosner et al. . |
| 4,876,242 | 10/1989 | Applebaum et al. . |
| 4,962,155 | 10/1990 | Fujita-Yamaguchi et al. . |
| 5,212,074 | 5/1993 | Kiefer et al. . |
| 5,260,200 | 11/1993 | Kahn et al. . |
| 5,401,830 | 3/1995 | McKenzie ................................ 530/371 |

OTHER PUBLICATIONS

Siegel et al, Journal of Biol. Chem., vol. 256, No. 17, pp. 9266–9273 (1981).
Dailey et al, Molecular and Cellular Biol., vol. 10, No. 12, pp. 6244–6256 (1990).
Kole et al, Biochemistry, vol. 30, pp. 682–688 (1991).
Kallen et al, Biochem. and Biophysical Res. Comm., vol. 168, No. 2, pp. 616–624 (1990).
Pessin et al, "Subunit Structure and Regulation of the Insulin–Receptor Complex," pp. 3–29. (1985).
Fujita–Yamaguchi et al, Journal of Biol. Chem., vol. 258, No. 8, pp. 5045–5049 (1983).
Jacobs et al, Biochem. and Biophys. Res. Comm., vol. 77, No. 3, pp. 981–988 (1977).
Cuatrecasas, Proc. Nat. Acad. Sci. USA, vol. 69, No. 5, pp. 1277–1281 (1972).
Pilch et al, Journal of Biol. Chem., vol. 255, No. 4, pp. 1722–1731 (1980).
Roth, "Assay of Peptide Hormones Using Cell Receptors: Application to Insulin and Human Growth Hormone", in *Hormone Assays*, pp. 66–81. (1975).
Rosen, Science, vol. 237, pp. 1452–1458 (1987).
McKenzie et al, The Journal of Cell Biology, vol. 111, No. 5, Part 2, p. 472A, Abstract #2642 (1990).
Goding, *Monoclonal Antibodies: Principles and Practice*, "Generation of Conventional Antibodies", Academic Press (London), 2nd Ed., 281–293 (1986).
McKenzie et al, Molec. Biol. Cell., vol. 3 (Suppl.), p. 141a, Abstract #819 (1992).
LeRoith et al, Experientia, vol. 42, pp. 782–788 (1986).
Kole et al, FASEB Journal, vol. 5, pp. 2728–2734 (Sep. 1991).
Lenard, TIBS–17, pp. 147–150 (Apr. 1992).
Schieven et al, Science, vol. 231, pp. 390–395 (Jan. 1986).
Blundell et al., Nature, vol. 287, pp. 782–787 (Oct. 1980).
Petruzzelli et al, J. Biological Chem., vol. 260, No. 30, pp. 16072–16075 (Dec. 1985).

*Primary Examiner*—Sheela Huff
*Attorney, Agent, or Firm*—Birch, Stewart, Kolasch & Birch, LLP

[57] ABSTRACT

A receptor for an insulin-like polypeptide is purified from yeast membranes. This "insulin receptor-like protein" has a structure analogous to that of the mammalian insulin receptor. The insulin receptor-like protein of *Saccharomyces cerevisiae* is a heterotetrameric glycoprotein. The protein has two polypeptide types, a first polypeptide which binds insulin and has an apparent molecular weight of 135,000 to 145,000 daltons and a second polypeptide which has an apparent molecular weight of 90,000 to 95,000 daltons and is phosphorylated on tyrosine in response to binding of insulin by said first polypeptide. The first and second polypeptides are joined by disulfide linkage. The protein requires a divalent metal ion for tyrosine autophosphorylation in response to binding of insulin. The yeast insulin receptor-like protein binds human insulin with a dissociation constant of $K_d = 8 \times 10^{-10}$ M and binds human insulin-like growth factor 1 with a $K_d = 4 \times 10^{-10}$ M.

19 Claims, 12 Drawing Sheets

METHOD FOR SCREENING COMPOUNDS FOR ACTIVITIES RELATED TO INSULIN RECEPTOR BINDING

CROSS REFERENCE TO RELATED APPLICATIONS

This application is a continuation of application Ser. No. 08/361,232 filed on Dec. 21, 1994, now abandoned, which was a divisional of application Ser. No. 07/956,290, filed on Oct. 5, 1992, now U.S. Pat. No. 5,401,830.

BACKGROUND OF THE INVENTION

1. Field of the Invention

The invention is directed to a purified insulin receptor-like protein. This receptor has some characteristics similar to mammalian insulin receptors and is therefore described herein as an "insulin receptor-like protein".

2. Description of the Related Art

Insulin, a central regulator of metabolism and mitogenesis, arose early in evolution. An insulin receptor-like protein and its gene in the fruit fly, *Drosophila melanogaster* and an insulin gene in the sponge *Geodia cydonium*, place the signaling pathway at or before the divergence between diploblastic and triploblastic animals during radiation of coelomates more than 560 to 540 million years ago (Ma). Insulin-regulated metabolic pathways such as glycolysis and glycogen synthesis are common to the five kingdoms, but an insulin-like signal transduction system in lower eukaryotes and prokaryotes remains controversial. Although conventional wisdom precludes the existence of hormone-like substances in species lacking a pancreas or other glands, the capacity for cell-cell communication via diffusible factors may have been integral to the genesis of more complex organisms consisting of various specialized tissues. Thus, an insulin receptor-like protein may be coupled to these molecules in *Saccharomyces cerevisiae* to trigger appropriate responses to extracellular nutrients and growth modulating stimuli.

Insulin and insulin-like molecules regulate diverse cellular processes of carbohydrate and intermediary metabolism, macromolecular synthesis, and mitogenesis. Phylogenetic distribution and regulation of ubiquitous biochemical pathways imply an evolutionarily ancient role for insulin-like hormones and their cognate receptors. *S. cerevisiae*, regarded as a slowly evolving species, possesses second messengers and mediators proposed to transduce the insulin signal in vertebrates, e.g. cyclic AMP, phosphodiesterases, serine/threonine and tyrosine-specific protein kinases, GTP-binding proteins and GTPase activating proteins, inositol phosphates, phosphatidylinositol kinases and phospholipases, and calcium-binding regulatory proteins (1,2,3). However, insulin signaling elements have never been confirmed in lower organisms. A protein endogenous to *Saccharomyces cerevisiae* which resembles the mammalian insulin receptor (IR) has been purified. Yeast IR-like protein (IRP) possesses a high molecular weight insulin binding domain and intrinsic tyrosine kinase activity.

The insulin family of hormones is widely distributed across the phyla. In addition to their occurrence in vertebrates, insulin-related receptors, binding proteins and ligands have been identified in organisms as diverse as the invertebrates *Drosophila melanogaster, Bombyx morii, Annelida oligocheta, Lymnaea stagnalis* and *Geodia cydonium*, higher plants such as spinach and *Lemna gibba* and the alga *Acetabularia mediterranea*, in the fungi *Neurospora crassa* and *Aspergillus fumigatus* protist *Tetrahymena pyriformis*, and in many bacteria, including *Escherichia coli, Halobacterium solinarium, Bordetella pertussiss* and *Acinetobacter calcoaceticus*. The insulin family of hormones has been documented extensively to control fundamental aspects of intermediary metabolic regulation, growth, differentiation and reproduction, which may explain the strong conservation of insulin-dependent signaling throughout the evolution of eukaryotes.

The vertebrate insulin receptor (IR) is a multifunctional heterotetrameric glycoprotein comprised of two 135 kD α-subunits that constitute the insulin binding domain and two 95 kD β-subunits with intrinsic tyrosine kinase activity (4). The structural and kinetic properties of the IR are similar in all vertebrate species and tissues studied, for instance, the neuronal IR has an α-subunit of 115–125 kDa and a β-subunit of 83 kDa. The stingray receptor has a homotetramer structure with a β-subunit of a 110 kD; the increase in molecular weight, compared to the vertebrate polypeptide, perhaps being due to glycosylation. These findings suggest that the insulin receptor protein is more highly conserved in evolution than its ligand. Furthermore, the IR is encoded by a modular gene, apparently assembled during evolution by successive joining of DNA seguences to encode specific functions in a multifunctional, multidomain protein synthesized, nevertheless, as a single-chain polypeptide.

An IR-like protein was identified in *D. melanogaster* with a subunit composition, tyrosine kinase activity, and functions in stimulation of carbohydrate metabolism, growth and differentiation throughout the life cycle of the fly identical to the mammalian counterpart. Furthermore, a protein that binds insulin with specificity, high affinity and some of the kinetic properties ascribed to the vertebrate receptor has been purified and partially characterized from a cell wall-less mutant of another ascomycete, *N. crassa*. However, the molecular weight of this *N. crassa* protein is not comparable to the vertebrate IR nor does it possess tyrosine kinase activity (5).

SUMMARY OF THE INVENTION

Components of the insulin secretory and signal transduction systems proposed in vertebrates occur in the yeast, *S. cerevisiae*. The presence of an insulin-like molecule and downstream effectors ascribed to the IR of higher eukaryotes suggests the existence of a cognate receptor endogenous to yeast. Some of these elements include cAMP, adenylate cyclase, and high and low $K_m$ phosphodiesterases, RAS and other GTP-binding proteins, GTPase-activating proteins, phosphoinositides and phosphatidylinositol kinases, calmodulin, numerous serine/threonine and tyrosine kinases, and respective phosphatases (6).

Specific, high affinity binding of insulin to intact cells and gradient purified plasma membranes was observed in wild-type and cell wall defective strains of *S. cervisiae* strain described in (7). The putative insulin receptor-like protein (IRP) from yeast was highly purified by detergent solubilization of the membrane fraction and sequential affinity chromatography on wheat germ agglutinin-agarose and insulin-agarose, techniques adapted from the purification of mammalian insulin receptors (IR). To improve recovery of IRP, yeast were harvested coincident with glucose exhaustion of the medium during the final generation in culture, a condition that parallels confluency of cultured mammalian cells when the IR is most abundant and displays highest affinity for insulin. The yeast were then washed in ultrafiltered medium to remove an endogenous insulin-like growth factor that may be associated preferentially with the receptor and could interfere with insulin-dependent assays used for detection of IRP throughout the isolation process. Despite these measures, purification of IRP proved challenging due to the exceedingly low number of insulin binding sites per cell, an intractable cell wall and extensive proteolytic activity in wild-type yeast. Radioreceptor assays and chromatographic techniques for the mammalian and Drosophila IR, adapted for yeast physiology, are described here for isolation and partial characterization of IRP from Saccharomyces.

The invention encompasses isolated IRP which binds insulin and insulin-like proteins. These ligands can be of mammalian or yeast origin. Binding of the ligand to the receptor of the present invention causes physiological changes in the yeast cell which alter its metabolism and growth.

The IRP is a heterotetrameric protein, having two α subunits of 135 to 145 kilodaltons molecular weight and two β subunits of 90 to 95 kilodaltons molecular weight. The binding site for the insulin-like protein ligand is in the larger subunit. Binding of an insulin-like ligand causes phosphorylation of at least one tyrosine residue in the smaller subunit. The larger subunits appears to be covalently joined by at least one disulfide bond to the smaller subunit.

The IRP requires a divalent metal ion, preferably manganese or magnesium, for the phosphorylation activity observed upon ligand binding to be expressed. Transition metal ions, particularly vanadate, are able to bind to the IRP and modulate the effects of ligand binding, at least with respect to phosphorylation of the small subunit of the receptor and some of the physiologic responses induced by the ligand in whole yeast cells. Vanadium compounds are being developed currently as insulinomimetic agents that exert a hypoglycemic effect in mammals.

In addition to providing the IRP protein, providing antibodies which specifically bind to IRP, proving a method for purifying the IRP from a yeast cell, providing chromatography matrices which comprise a bead conjugated to the IRP and providing methods for identifying and purifying proteins which function "downstream" of the ligand-receptor complex in intracellular signaling processes regulated by insulin-like proteins, and providing methods for identifying drugs which interfere with the ligand-receptor complexation and downstream signaling processes are all objects of the present invention.

The present invention also encompasses methods for screening compounds for anti-mycotic activity. Such methods comprise contacting the compound to be screened with a protein of *Saccharomyces cerevisiae* that binds insulin with a $K_d$ of about $8 \times 10^{-10}$ M, and comprises a heterotetramer. The heterotetramer contains two dimers, wherein each dimer comprises a first polypeptide which binds insulin and has an apparent molecular weight of 135,000 to 145,000 daltons as determined by SDS-polyacrylamide gel electrophoresis and a second polypeptide which has an apparent molecular weight of 90,000 to 95,000 daltons as determined by SDS-polyacrylamide gel electrophoresis and is phosphorylated on tyrosine in response to binding of insulin by said first polypeptide. Then one determines if the contacting step alters a biochemical activity of the protein. Preferred biochemical activities to be assayed are insulin binding, tyrosine phosphorylation of the second (90–95 kDa) subunit, and activities of downstream proteins, especially their tyrosine phosphorylation.

Application Ser. No. 07/956,294, filed Oct. 5, 1992, now abandoned and U.S. Pat. No. 5,670,618, issued on Sep. 23, 1997, which is a continuation of application Ser. No. 07/956,342, filed Oct. 5, 1992, now abandoned describe related subject matter. The entire contents of these is hereby incorporated by reference.

BRIEF DESCRIPTION OF THE DRAWINGS

FIG. 7A shows insulin-binding activity of the IRP. Radioactive insulin was cross-linked to the 135 kDa polypeptide after binding to equilibrium, as demonstrated by reducing SDS-PAGE. In non-reducing gels, the radioactivity is associated with a 350–400 kDa protein. FIG. 7B shows the tyrosine kinase activity demonstrated by autophosphorylation of the IRP in the presence (+I) or the absence (−I) of insulin.

DETAILED DESCRIPTION OF THE INVENTION

Figure 1:
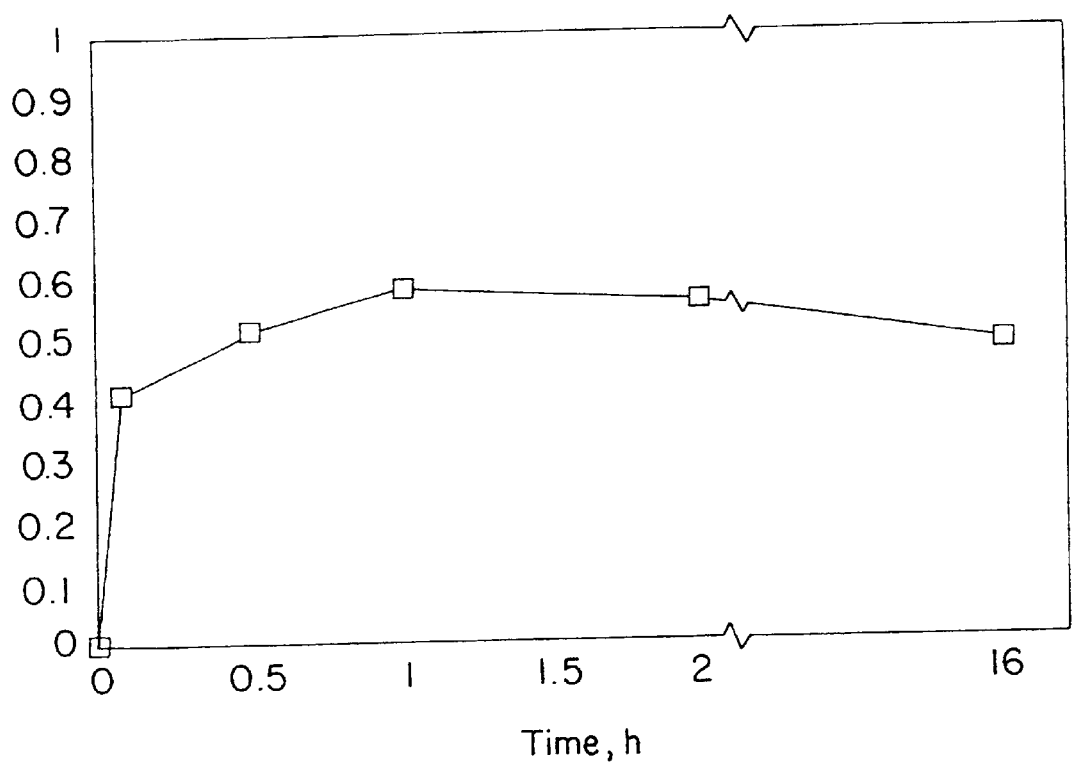
FIG. 1 shows insulin binding to IR-like protein.

The preferred embodiments of the invention are described by means of the following examples. These examples are intended to be illustrative, rather than limiting in scope.

It is to be understood that subfragments or variants of the insulin-like protein receptor protein disclosed in the present application wherein the original amino acid sequence is modified or changed by insertion, addition, substitution, inversion or deletion of one or more amino acids are within the scope of the present invention, so far as they retain the essential ligand-binding specificity and biochemical activities described herein.

Abbreviations used throughout this application are: IRP, insulin receptor-like protein; HEPES, 4-(2-Hydroxyethyl)-1-piperazineethanesulfonic acid; PEG, polyethylene glycol; IGF-I, insulin-like growth factor I; IGF-II, insulin-like growth factor II; EGF, epidermal growth factor, TGF-α, transforming growth factor (alpha); α-MF, alpha-mating factor; SDS, sodium dodecyl sulfate; PIC, protease inhibitors cocktail; PMSF, phenylmethylsufonyl fluoride; TPCK, N-tosyl-L-phenylalanine chloromethyl ketone; EGTA, ethylene glycol-BIS-(β-aminoethyl ether) N,N,N',N'-tetraacetic acid; p-APMSF, 4-amidinophenylmethanesulfonyl fluoride; DTT, dithiothreitol; β-ME, 2-mercaptoethanol; HRP, horseradish peroxidase; WGA, wheat germ agglutinin; BCA, bicinchoninic acid; TCA, trichloroacetic acid; PIC, protease inhibitor cocktail (1X); YNB, yeast nitrogen base medium; YPD, yeast extract, peptone, dextrose medium; RIA, radioimmunoassay; ECL, enhanced chemiluminescence; DSS, disuccinimidyl suberate.

General Materials and Methods

Materials

All chemicals were of reagent grade or higher purity. Microbiological culture media were purchased from Difco. Cell culture grade glucose and amino acids, buffers, sucrose (Grade I), carbonyl and peroxide-free TRITON X-100, protease inhibitors (TPCK, PMSF, benzamidine, leupeptin, bestatin, pepstatin A, soybean trypsin inhibitor, $\epsilon$-amino-n-caproic acid, chymostatin, Trasylol, p-APMSF), EGTA, bovine gamma globulin, bovine and porcine insulin (both approximately 24 I.U. per mg; 0.5% zinc), porcine proinsulin, yeast $\alpha$-MF, TGF-$\alpha$, and insulin-agarose were obtained from Sigma Chemical Co. IGF-I, IGF-II, and EGF (all human recombinant) were purchased from Boehringer-Mannheim. Bacitracin was from Paddock Laboratories, Inc. WGA-agarose was obtained from Sigma Chemical Co. or from Miles Yeda, Ltd. Fatty acid-, nuclease- and protease-free bovine serum albumin (Fraction V; RIA-grade with less than 1 unit insulin per g) was available from Calbiochem. Monoiodinated porcine [$^{125}$I]insulin (receptor grade) was obtained from New England Nuclear. Disuccinimidyl suberate and the BCA protein determination kit were purchased from Pierce. Electrophoresis grade SDS, glycine, polyacrylamide, bis-acrylamide, nitrocellulose paper, Bradford protein assay kit, silver staining kit, unstained and pre-stained high molecular weight range markers were purchased from Bio-Rad. Coomassie Brilliant Blue 250-R was from Fisher. Monoclonal antiphosphotyrosine antibody (4G10) was obtained from Upstate Biotechnology, Inc. Sheep anti-mouse Ig-HRP secondary antibody conjugate and the ECL chemiluminescence detection system for Western blotting were supplied by Amersham. X-Omat AR film for autoradiography was from Kodak. Nitrocellulose membranes for ultrafiltration (ULTRAFREE; nominal exclusion 10 kDa) were purchased from Millipore. Glass beads (0.5 mm diameter) were obtained from Denville Scientific.

Culture of Yeast Cells

The haploid *S. cervisiae* wild-type strain S288c (MAT$\alpha$ SUC2 mal mel gal2 CUP1) (ATCC 26108, American Type Culture Collection, Rockville, Md.) and cell wall defective *S. cerevisiae* mutant strain LBl-16A (MAT$\alpha$ mnn2 SUC2 mal mel gal2 CUP1), both obtained from the Yeast Genetic Stock Center (University of California, Berkeley), were used for binding studies and isolation of IRP. Stock cultures were maintained on YPD (1% (w/v) yeast extract, 2% (w/v) peptone, 2% (w/v) glucose) plates for less than one month. Starter cultures were prepared by transferring cells to defined YNB medium (1.7 g/liter), pH 5.4, supplemented with 2% (w/v) glucose, 5 g/liter ammonium sulfate, 10 mg/liter histidine, 20 mg/liter methionine and 20 mg/liter tryptophan and were incubated at 30° C. with shaking (250 rpm) until cells were in exponential phase ($3\times10^6$ cells/ml; $A_{600}=0.1$) of growth.

Protease Inhibitors Cocktail (PIC)

An aqueous stock solution (10 X) was prepared as previously reported (70) and contained 1 mg/mL bacitracin, 0.2 mg/mL soybean trypsin inhibitor, 0.1 mg/mL bestatin, 50 $\mu$g/mL pepstatin A, 50 $\mu$g/mL leupeptin, 20 $\mu$g/mL chymostatin, 20 mM benzamidine, 10 mM p-aminobenzamidine, 10 mM $\epsilon$-amino-n-caproic acid, 10 mM EGTA, 10 mM EDTA, 10 mM p-APMSF (for steps performed at pH 8.0), 5 mM TPCK. 10 mM PMSF (when pH 6.5 buffer is used) was dissolved in isopropanol and added to PIC, which was freshly prepared and filter-sterilized before use. When indicated, 5 mM iodoacetamide was included during bead-beating.

Deproteinized Conditioned Medium

Cells were harvested coincident with glucose exhaustion of the culture medium by tangential flow filtration through a Pellicon 0.45 $\mu$m unit. Filtered medium was passed again through a 0.4 $\mu$m filtration unit (Nalgene) to eliminate residual cells and debris, and loaded into 60-mL syringes fitted with 9 kDa nominal exclusion ultrafilters (Millipore) on a compact infusion pump (Harvard Apparatus, Inc.) operating at room temperature. Ultrafiltered medium was used immediately to wash cells for isolation of IRP.

EXAMPLE 1

Equilibrium Binding of $^{125}$I-insulin and $^{125}$I-IGF-I to Whole Yeast Cells and Partially Purified Membranes 1. Equilibrium Binding to Intact Yeast Cells Starter cultures were inoculated into YNB medium plus 2% (w/v) glucose and amino acids as described above, and grown to early or late exponential phase, or to stationary phase (approximately $10^8$ cells/ml; $A_{600}=8-10$). Cells were harvested by centrifugation at 1,000 X g for 20 min at 25° C. and washed in the same medium without glucose. Supernatants were decanted and cell pellets resuspended in Eppendorf tubes containing binding buffer (100 mM HEPES, pH 7.6, 120 mM KCl, 1.2 mM MgSO$_4$, 2.5 mM NaCl, 10 mM glucose, 15 mM sodium acetate, 1 mM EDTA, 10 mg/mL RIA-grade BSA) modified from Roth (8) and 0.1 nM (approximately 30,000 CPM) of porcine [$^{125}$I]insulin in the absence or presence of $1\times10^{-7}$ M porcine or bovine insulin. To maximize specific binding and displacement of the radiolabeled ligand, preliminary trials were performed with S288c yeast in the presence of various concentrations of glucose in the wash medium and binding buffer (Table 1). Likewise, the concentration of sodium ions in the binding buffer was reduced and potassium ions were increased to be more compatible with yeast physiology. In addition, cell number was increased to $1\times10^8$/ml and the assay was performed at 4° C. until equilibrium was reached at 2 h (FIG. 1). Binding was terminated at various times by pelleting cells at 13,000 x g for 2 min at 4° C. and washing twice with ice-cold binding buffer. The tips of the tubes were excised and pellet associated radioactivity quantitated in a TM Analytic gamma counter for 5 min. Tracer degradation was examined in the absence and presence of $1\times10^{-7}$ M unlabelled porcine insulin, and quantitated by precipitation of an aliquot of post-incubation supernatant with ice-cold 10% (w/v) TCA. Corrections for non-specific binding (2–3% of the total) and insulin degradation (less than or equal to 5% of the tracer in the assay) were included in calculations of the number and affinity constants of insulin binding sites. Cell viability (greater than 95%) following assay was verified by trypan blue exclusion and plating on YPD medium.

2. Preparation of Plasma Membranes

Yeast strain S288c was grown to early logarithmic phase in 60 liters of YNB medium supplemented with 2% (w/v) glucose and amino acids at 30° C. for 13 hours. Cells were concentrated by tangential flow filtration in a Pellicon 0.45 $\mu$m unit (Millipore), pelleted by low speed centrifugation (1500 X g) at room temperature, and washed in YNB medium lacking glucose, amino acids and ammonium sulfate. Washed cells (9.9 g wet weight) were centrifuged at low speed and resuspended in 100 ml ice-cold 1 mM EDTA, pH 4.2. Cells were centrifuged again at 4° C. for 5 min and resuspended in 10 mL of 17% (w/v) sucrose and 1 mM EDTA, pH 4.2, and 20 ml of glass beads. The cell suspension was homogenized by bead-beating in an ice-jacketed apparatus (Biospec Products, Bartlesville, Okla.) for 3 min with two-30 sec bursts and twelve 10 sec bursts with 3 min periods of cooling between each. Cell breakage was estimated at 75% by light microscopy. The homogenate was diluted 1:1 with 1 mM EDTA and centrifuged for 10 min at 1500 x g at 4° C. in a Sorvall SS-34 rotor to remove unbroken cells and debris. Approximately 6 mL of the supernatant was loaded onto 50 mM Tris buffered (pH 7.5) linear sucrose gradients [10–65% (w/v)] for isopycnic centrifugation at 265,000 X g in a Beckman 70Ti rotor for 21 h at 4° C. The gradients were fractionated at 4° C. from the bottom in 1-ml aliquots and analyzed for protein concentration by the BCA method (against Tris-sucrose gradient blanks) and for chitin synthetase activity as described (9). Fractions at a specific gravity of 1.20–1.22, coincident with a peak of chitin synthetase activity, were pooled and stored at −80° C. for subsequent assay of insulin binding and tyrosine phosphorylation of endogenous, membrane-associated proteins.

3. Insulin Binding to Solubilized and WGA-Purified Plasma Membranes

Aliquots of yeast plasma membranes were diluted in and ultracentrifuged at 130,000 x g for 30 min at 4° C. to remove sucrose. Resuspended membranes (44 mg protein/ml) were solubilized on ice for 30 min in 10% TRITON X-100, 50 mM HEPES, pH 7.5, 1 mM EDTA, 1% Trasylol and PIC. Solubilized membranes were diluted to 7–8 mg protein/ml in 50 mM Tris/HCl, pH 7.5, 1% Trasylol, PIC, 0.05% TRITON X-100, 0.5% BSA (Fraction V). An equal volume of [$^{125}$-I]-labeled insulin or IGF-I, diluted in the buffer above, was added in the presence of excess hormone to the solubilized membranes in a final volume of 210 μl and incubated overnight at 4° C. The binding was terminated by addition of 25% PEG to solubilized membranes (9:1 vol/vol). For chromatography on WGA-agarose, membranes (5–6 mg protein/ml) were solubilized for 3 h on ice in 50 mM HEPES, pH 7.5, 150 mM NaCl buffer plus PIC containing 1% TRITON X-100. The mixture was centrifuged at 130,000 x g for 45 min at 4° C. and the supernatant was applied three successive times to a WGA-agarose column (2 ml). The column was washed with the HEPES-salt buffer plus 0.1% TRITON X-100 and the adsorbed material was eluted in 1 ml fractions with 0.3 M N-acetylglucosamine in the same buffer. Protein concentration of the eluates was assessed with the Bio-Rad assay using 50 mM HEPES, pH 7.5, 150 mM NaCl buffer containing 0.1% TRITON X-100 and 0.3 M N-acetylglucosamine. Insulin binding to WGA-agarose purified protein was studied by incubating 25 μl of sample with 100 μl [$^{125}$I] insulin (0.03 nM), 25 μl of 50 mM HEPES, pH 8.0, 150 mM NaCl overnight at 4° C. in the presence of indicated concentrations of porcine insulin. The final incubation volume (200 μl) also 1% BSA and 1 mg/ml bacitracin. To terminate the incubation, 100 μl of 0.3% bovine gamma globulin and 300 μl of 25% PEG were added to the tubes and centrifuged at 2500 x g for 15 min at 4° C. The pellet was washed once with 300 ml of 12.5% PEG, the supernatant was aspirated and the radioactivity was quantitated in a gamma counter.

The presence of high affinity binding sites on the surface of intact cells of wild-type strain S288c and cell wall defective mutant LB1-16A was demonstrated using a modification of the radioreceptor assay described by Roth (8). Specific binding of insulin to exponential phase S288c and LB1–16A cells was dependent on the nutrient composition of the medium (Table I).

TABLE I

Effect of Glucose on Specific Binding of Insulin to Intact Yeast

| Wash Buffer (110 mM Glucose) | Binding Buffer (10 mM Glucose) | Binding/ Displacement |
| --- | --- | --- |
| + | + | +/− |
| − | + | +/+ |
| + | − | −/− |
| − | − | −/− |

Pellets of S288c cells were washed in fresh YNB medium without supplements and with indicated concentrations of glucose. The binding assay was conducted as described above.

Figure 2:
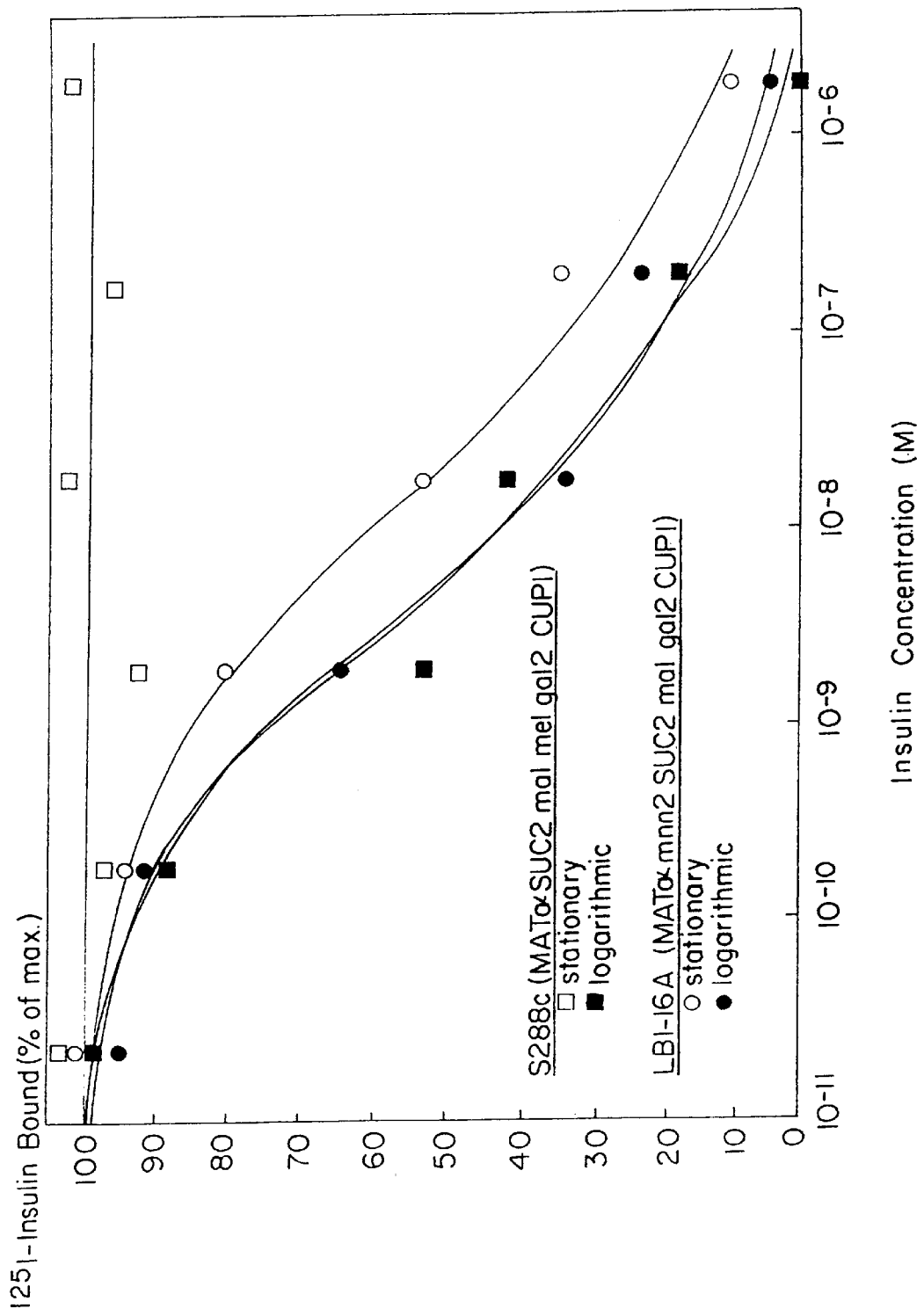
FIG. 2 shows insulin binding profiles for strains S288c and LB1-16A.

When cells were washed in the absence of glucose and nitrogen sources (YNB minus ammonium sulfate and amino acids), and incubated in the presence of a low concentration of glucose (10 mM) in the binding buffer, total binding accounted for 2–3% of the tracer added and, of this, approximately 0.5% represented specific binding. Apparent equilibrium was achieved after 1–2 h of incubation at 4° C. (FIG. 1). Displacement of insulin tracer could be observed over five orders of magnitude of insulin concentrations with 50% bound to intact cells at approximately $5+10^9$ M insulin (FIG. 2). Although specific binding and displacement could not be demonstrated with stationary phase cells of S288c, even at concentrations of insulin higher than $1 \times 10^6$ M, [$^{125}$I]insulin bound to LB1-16A cells in the stationary phase was displaced by 50% at approximately $2 \times 10^{-8}$ M unlabeled ligand (FIG. 1). Scatchard analyses of binding to exponential phase cells revealed a curvilinear plot, which indicated negative cooperativity or multiple classes of binding sites, one class with high affinity and low number and another with reciprocal properties. The high affinity insulin binding sites had an apparent Kd between 0.75 to 0.9 nM.

Figure 3:
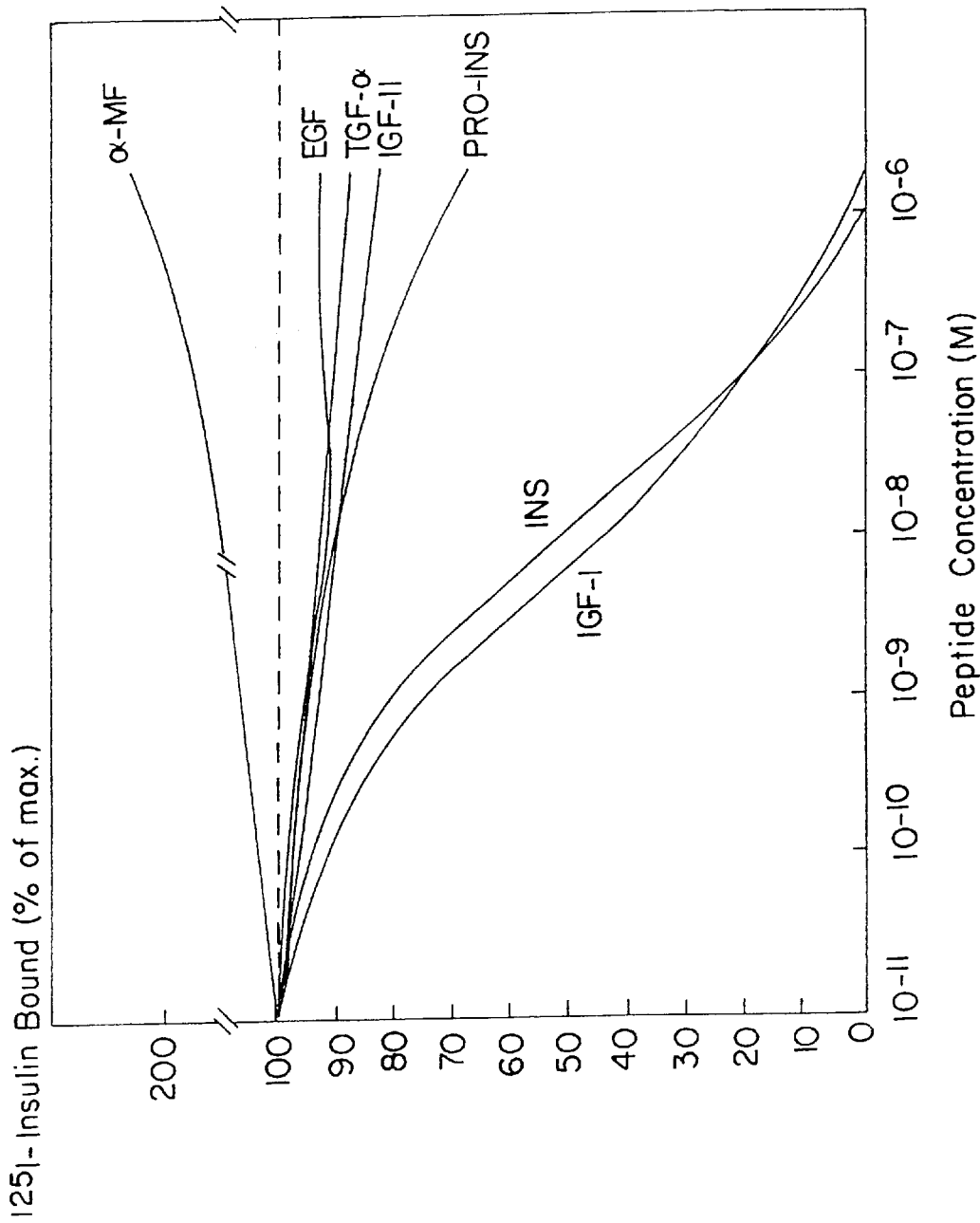
FIG. 3 shows specificity of insulin binding to *S. cerevisiae*.

Various insulin-like peptides and unrelated molecules were evaluated for the ability to displace [$^{125}$I]insulin from exponential phase, wild-type cells (FIG. 3). Of the ligands tested, insulin and IGF-I were equally effective. Proinsulin could displace approximately 30% of the tracer at $1 \times 10^6$ M, whereas IGF-II, TGF-α, and EGF failed to displace [$^{125}$I] insulin. Increasing concentrations of the yeast α-mating factor in the binding assay almost doubled the amount of insulin tracer binding to intact S288c cells of the α-mating type.

Figure 4:
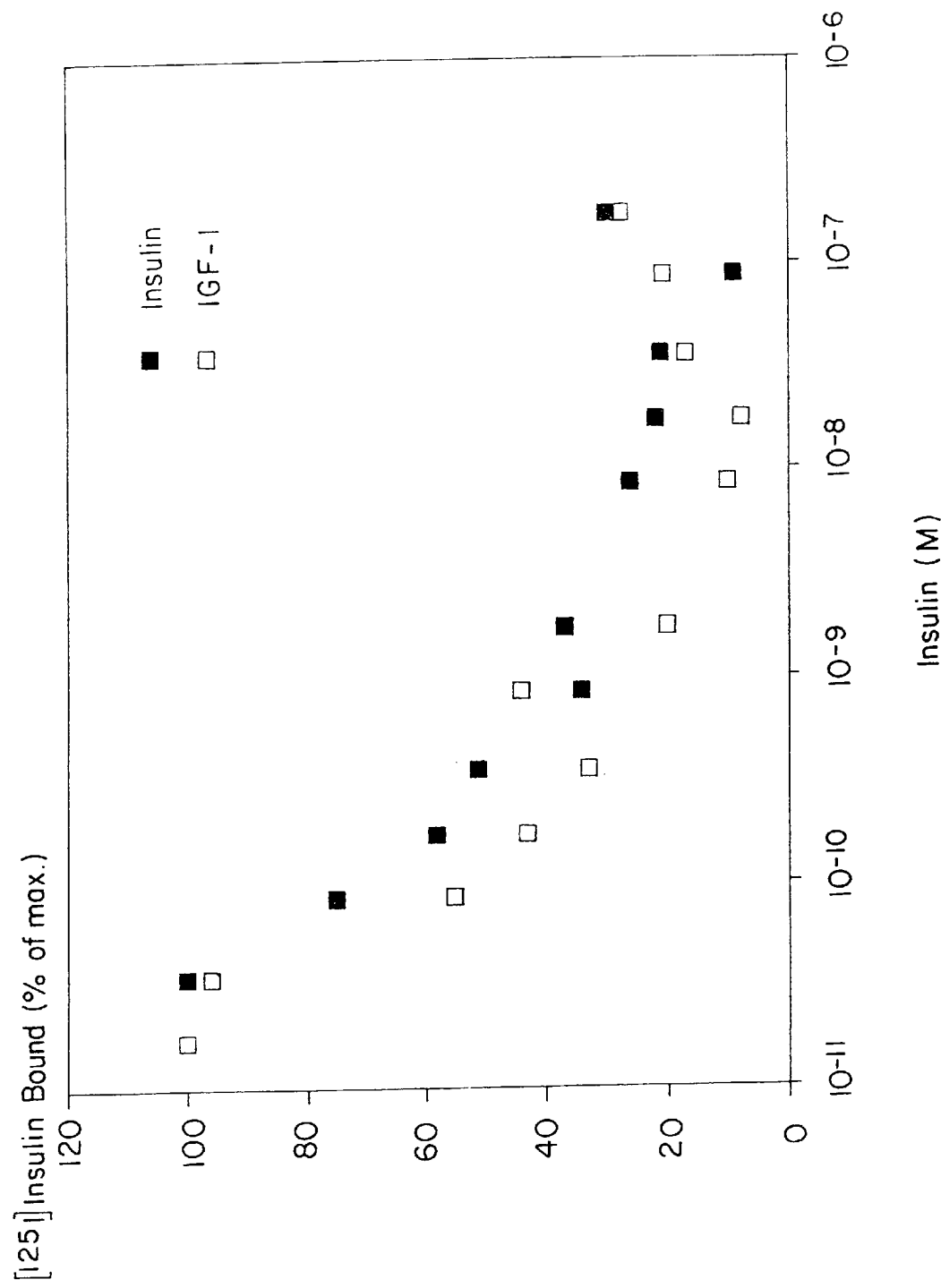
FIG. 4 shows displacement of [$^{125}$I] insulin from plasma membranes.

Specific binding of insulin and IGF-I was also localized on sucrose-gradient purified, detergent solubilized plasma membranes, from exponential phase wild-type cells (FIG. 4). In these experiments, total binding accounted for 3–4.5% of the added counts and specific binding represented 0.7–1.1% of the total. Scatchard analyses indicated a curvilinear plot and at least two different classes of binding sites, as observed in intact cells (FIG. 3). The high affinity class had an apparent $K_d$ of 0.4 nM for insulin and represented $6 \times 10^9$ sites per mg of protein. The low affinity class exhibited an apparent $K_d$ of 90 nM and accounts for $9 \times 10^{11}$ sites per mg of protein.

IGF-I specifically bound plasma membranes and the high affinity sites demonstrated a lower apparent $K_d$ of 0.25 nM which translates into $4 \times 10^9$ sites per mg of protein. The low affinity IGF-I binding sites had an apparent $K_d$ of 15 nM and $1 \times 10^{11}$ sites per mg of protein. Collectively, the studies on intact cells grown to exponential phase and plasma membranes isolated from them, suggested the presence of 20–200 high affinity binding sites per cell for insulin and IGF-I. Insulin and IGF-I receptors in mammals apparently derive from a common ancestral molecule and share cross-reactivity of their respective ligands, subunit compositions, and the ability to autophosphorylate in response to hormone binding.

Total binding of insulin to gradient purified membranes adsorbed to a WGA-agarose column equilibrated at pH 8.0 after solubilization was approximately 4.2% of the counts added. However, binding of the tracer to this sample in the presence of $1 \times 10^{-6}$M insulin represented 4.5% of counts added to the incubation mixture; i.e. specific binding could not be detected under these conditions. At pH 6.5, 0.7% of the counts added were specifically bound to WGA-purified protein in the presence of excess unlabeled insulin. Conversely, total binding of $[^{125}I]$ IGF-I increased to nearly 8%, and specific binding accounted for 1.7% of counts detected in the presence of $1 \times 10^{-6}$M unlabeled IGF-I or insulin. Specificity of IGF-I binding was not apparently dependent upon pH between values of 6.5 and 8.0.

EXAMPLE 2

Purification of the Insulin-like Receptor Protein from Yeast

For receptor isolation, cells from starter cultures were transferred to a total volume of twenty to forty liters of the same medium and incubated as above. When the culture reached $A_{600}$=4, the glucose content of the medium was monitored with immobilized glucose oxidase strips (Ames Diagnostics; Elkhart, Ind.) and, coincident with glucose exhaustion prior to early stationary phase ($A_{600}$=6–8), cells were harvested by tangential flow filtration. Filtered cells were collected by centrifugation at 3000–3500 X g for 30 min at room temperature, washed once as above in conditioned medium deproteinized by ultrafiltration and supplemented with PIC. Washed cells (approximately 100 g wet weight) were diluted 1:1 with ice-cold 50 mM MOPS buffer, pH 6.5, supplemented with PIC, and disrupted by bead beating in an ice-jacketed apparatus with seven or eight one-minute bursts, each interrupted by a three-minute cool-down period. Cell breakage, as determined by microscopy and liberation of soluble protein was estimated at >95%. From this step on, all manipulations were conducted at 4° C. and fractions were maintained on ice. The broken cell preparation was centrifuged at 5000 x g for 30 min, to remove wall and organelle debris. The post-mitochondrial supernatant was centrifuged immediately at 130,000 x g for one hour in a Sorvall SW Ti41 rotor. Pellets, consisting of the crude membrane fraction, were resuspended in 2% (v/v) TRITON X-100 (peroxide and carbonyl free), 50 mM MOPS buffer, pH 6.5, and PIC, and were incubated on ice for 30 min. The suspensions were centrifuged at 130,000 x g for 1 h to recover the detergent-solubilized proteins. Solubilized membranes, adjusted to 0.2% (v/v) TRITON X-100, in 50 mM MOPS, pH 6.5 or 8.0, containing 5 mM $MgCl_2$ and PIC, were applied at a rate of 2.5 ml/min to a WGA agarose column (1 mL), equilibrated in the same buffer. The column was washed, excess buffer removed by gravity and the semi-dry WGA-agarose matrix was eluted by soaking for 30 min in 1-mL of equilibration buffer (50 mM MOPS, pH 6.5 plus 0.1% (v/v) TRITON X-100 and PIC) containing 0.3 M N-acetylglucosamine and recovered by gravity flow as above. The WGA fraction was adsorbed for 30 min to an insulin-agarose matrix (0.5–1 ml) packed in a tuberculin syringe, equilibrated in 50 mM MOPS, pH 8.0 plus 0.1% (v/v) TRITON X-100 and PIC. The eluate was recycled at least ten times through the column. The material retained in the syringe column was eluted with 1-mL of 1 M, 0.1% TRITON X-100, 50 mM sodium acetate, pH 5.3. Immediately after elution, the IR-like protein was assayed for insulin binding and tyrosine kinase activity.

Figure 5:
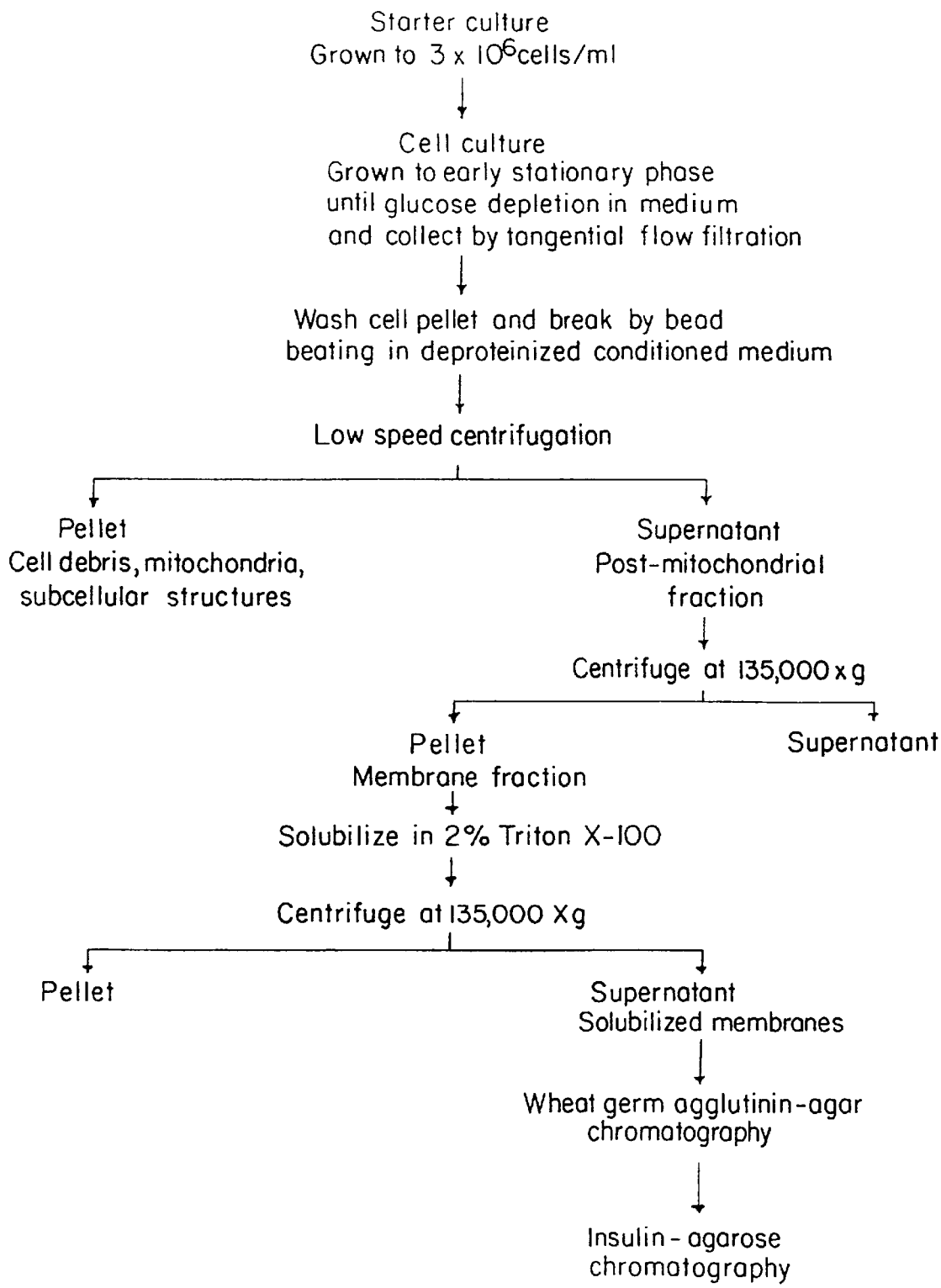
FIG. 5 shows a flowchart of IRP purification.

To obtain purified IRP from yeast membranes, an isolation procedure (illustrated in FIG. 5) was developed by adapting classical methods for the vertebrate IR (10–14). A typical purification of IRP from 20 liters of yeast (100 g packed wet weight of cells; 25 g of protein) yielded 200 ng of protein, and is summarized in Table II.

TABLE II

PURIFICATION OF S. CEREVISIAE INSULIN RECEPTOR LIKE-PROTEIN

| Fraction | Total volume (ml) | Total protein (mg) | Total activity fmol bound | Specific activity fmo/mg | Purification x-fold | Yield (%) |
|---|---|---|---|---|---|---|
| Crude membranes | 23 | 228 | 5.1 | 0.004 | 1 | 100 |
| Solubilized membrane | 19 | 8.25 | 3.6 | 0.043 | 20 | 71 |
| Wheat germ agglutinin | 1 | 0.08 | 3.5 | 4.35 | 1964 | 68 |
| Insulin-agarose | 0.7 | 0.0004 | 2.3 | 575 | 264000 | 44 |

The final purification factor relative to the crude membranes is 264,000-fold with exceptional enrichment achieved in the two affinity chromatography steps (Table II, steps 3 and 4).

Figure 6:
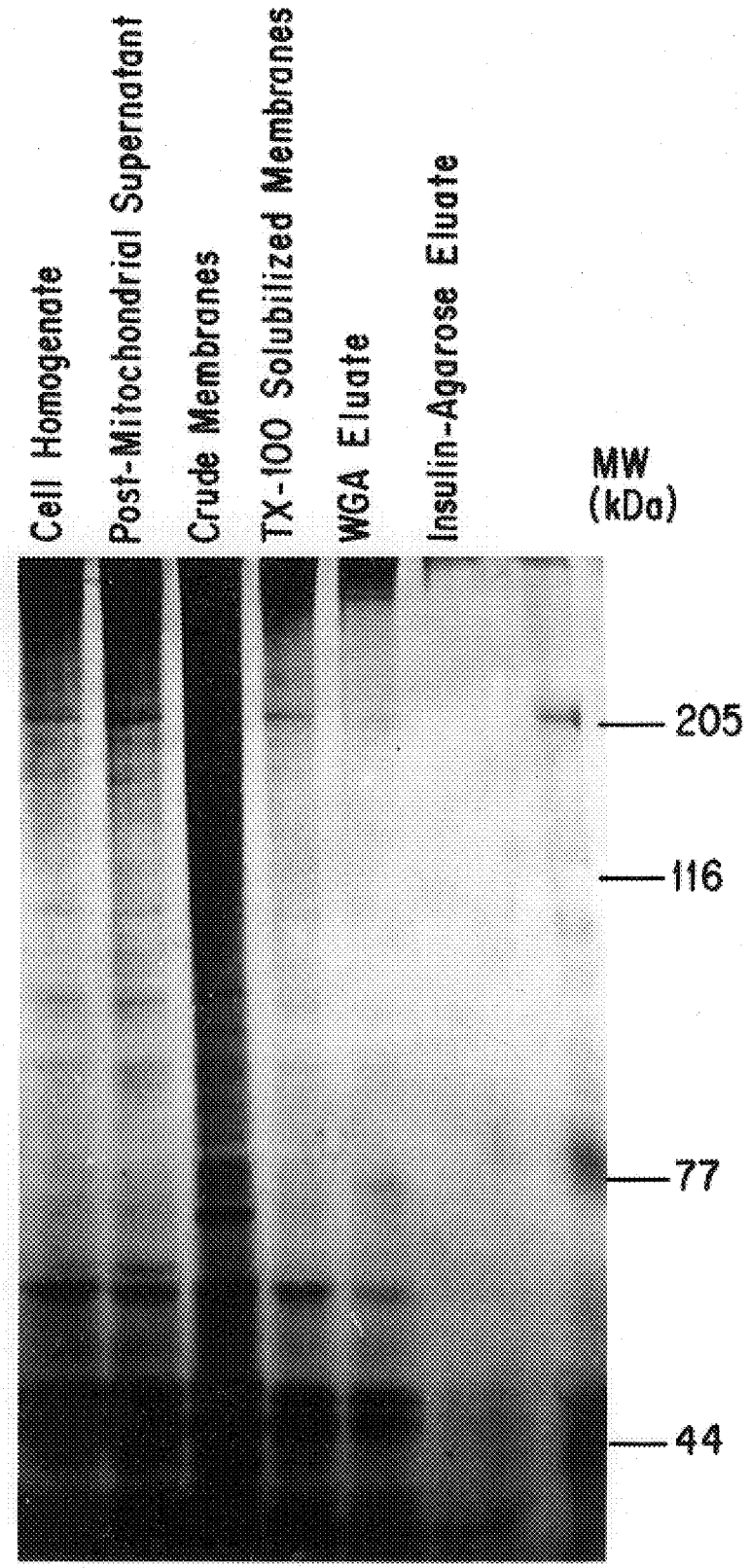
FIG. 6 shows samples taken along the purification procedure, electrophoresed and stained with silver and Coomassie Brilliant Blue-R.

Analysis by reducing SDS-PAGE at each step of isolation demonstrated increasing purity (FIG. 6). At the final step of purification on insulin-agarose, IRP is estimated to be 90% homogeneous, as visualized by silver staining of nonreducing gels. In addition, the mass recovery, as measured by BCA and predicted from the number of detectable binding sites in purified plasma membranes and intact cells, is quite low. In reducing gels, signals corresponding to subunits of IRP could not be visualized by Coomassie or silver staining methods, confirming previous reports of difficulty detecting purified receptor subunits by these techniques (12,13). However, BCA staining of gels in situ yielded a faint signal at approximately 95 kDa at the ultimate step of purification, and indicated a discrepancy between the methods of protein quantitation.

EXAMPLE 3

Binding of Insulin to Purified IRP and Tyrosine Phosphorylation of the IRP in Response to Insulin Binding 1. Binding of Insulin to Isolated IRP Aliquots 10 ng of purified IRP were incubated with 0.1 nM (30,000 CPM) receptor grade porcine $[^{125}I]$insulin in the presence and absence of $1 \times 10^{-6}$ M unlabelled insulin. The pH of the incubation buffer was varied between 6.5 and 8.0 to identify appropriate conditions for binding and crosslinking of ligand to the purified receptor. After 16 h of incubation at 4° C., the IR-like protein and ligand were crosslinked for 45 min with 0.3 M disuccinimidyl suberate (15). Samples were treated with 4x sample buffer containing 5% (v/v) β-mercaptoethanol, boiled for five min, loaded onto a 7.5% (w/v) polyacrylamide gels and electrophoresed according to Laemmli (16). The gel was dried and exposed to X-Omat film for five days at −80° C. to display labeled bands.

To compare binding of insulin to IRP at each step of purification, samples of fractions were incubated with porcine [$^{125}$I]insulin in the presence of $10^{-6}$ M hormone until equilibrium was reached and crosslinked to the tracer, as described above. Samples were electrophoresed under non-reducing conditions in 7.5% (w/v) polyacrylamide gels. Companion gels were Coomassie and silver stained or cut in 0.5 cm pieces which were counted in a TM Analytic Gamma Counter for 5 min. Protein concentrations were determined by longitudinal scanning of the stained gel and referenced to known quantities of molecular weight standard proteins.

2. Measurement of Intrinsic Tyrosine Kinase Activity of IRP

Highly purified IRP was added immediately to two reaction pools containing 50 μM ATP, 5 mM $MnCl_2$, 50 mM MOPS buffer, pH 6.5, with or without $10^{-7}$ M bovine insulin (24 I.U./mg; 0.5% Zn), preincubated at 30° C. for 30 min. IRP phosphorylation reactions were initiated by addition of aliquots of 10–20 ng of protein to the reaction pools and incubated at 30° C. The reaction was stopped at indicated times by dispensing aliquots to boiling 4x sample buffer; the mixtures were further boiled for 5 min. Samples were reduced with 5% (v/v) β-mercaptoethanol, and electrophoresed in 7.5% (w/v) SDS-polyacrylamide gels. Proteins were electrophoretically transferred to a nitrocellulose membrane that was blocked with 5% (w/v) non-fat dry milk in TTBS (20 mM Tris, 137 mM NaCl, 0.1% (v/v) Tween-20). Monoclonal antiphosphotyrosine antibody 4G10 (Upstate Biotechnology, Inc.) was added at a 1:2,500 dilution and incubated 4–12 h. Following incubation with the primary antibody, sheep anti-mouse Ig-HRP whole antibody was used at a 1:10,000 dilution, and the signal from phosphotyrosine-modified proteins developed with the ECL chemiluminescence system was detected by exposure of blots to Kodak X-Omat film.

Figures 7A, 7B:
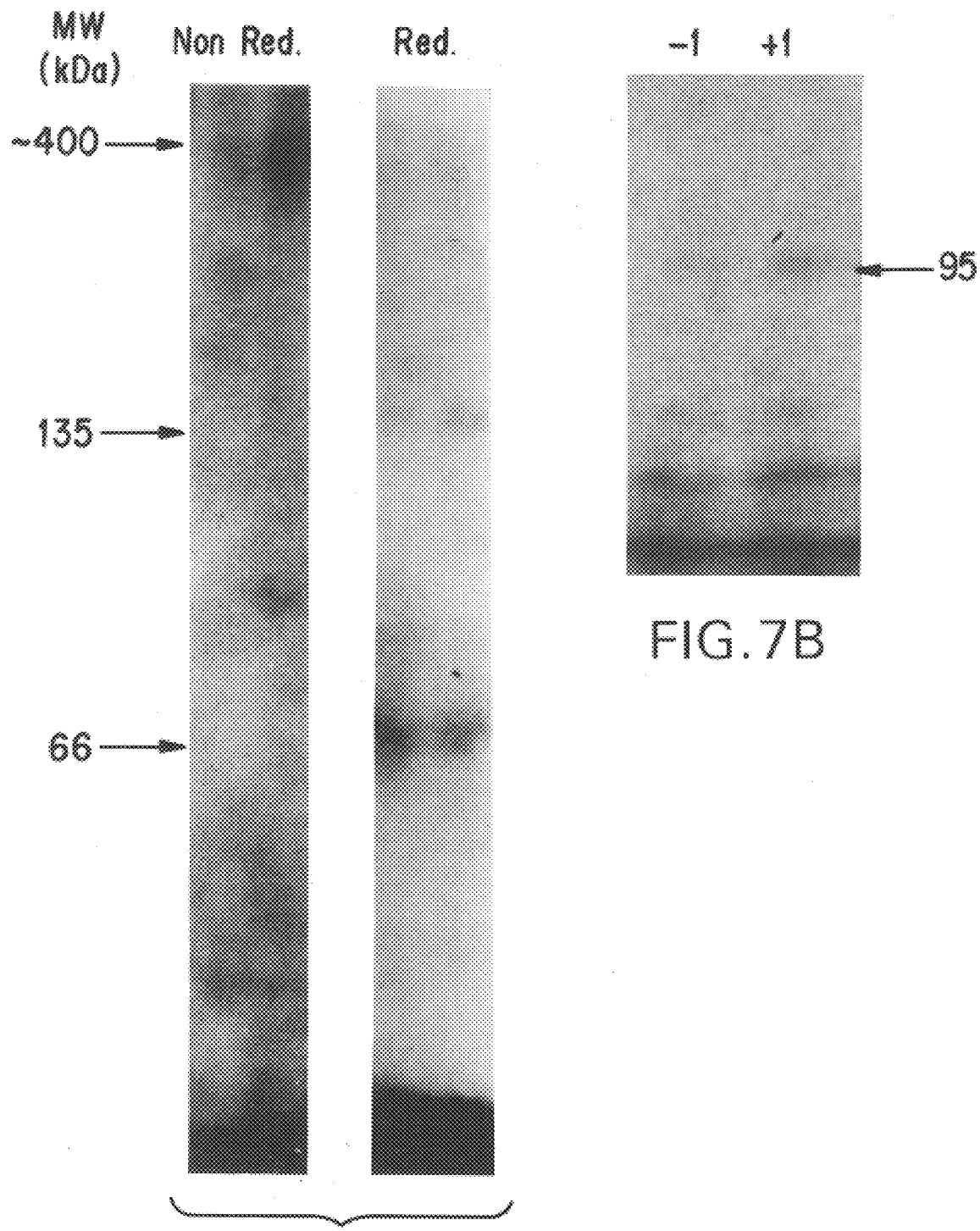
FIGS. 7A and 7B show insulin binding activity of the IRP.

To characterize the putative receptor, highly purified IRP was incubated with [$^{125}$I]-insulin until equilibrium was reached, crosslinked to the ligand, electrophoresed under non-reducing conditions and autoradiographed to determine the molecular weight of the complex. Under nonreducing conditions, crosslinked [$^{125}$I]insulin migrated exclusively with a diffuse species at 300–400 kDa, but visualization of the complex was inhibited by excess unlabeled insulin in the reaction mixture (FIG. 7a).

Figure 8:
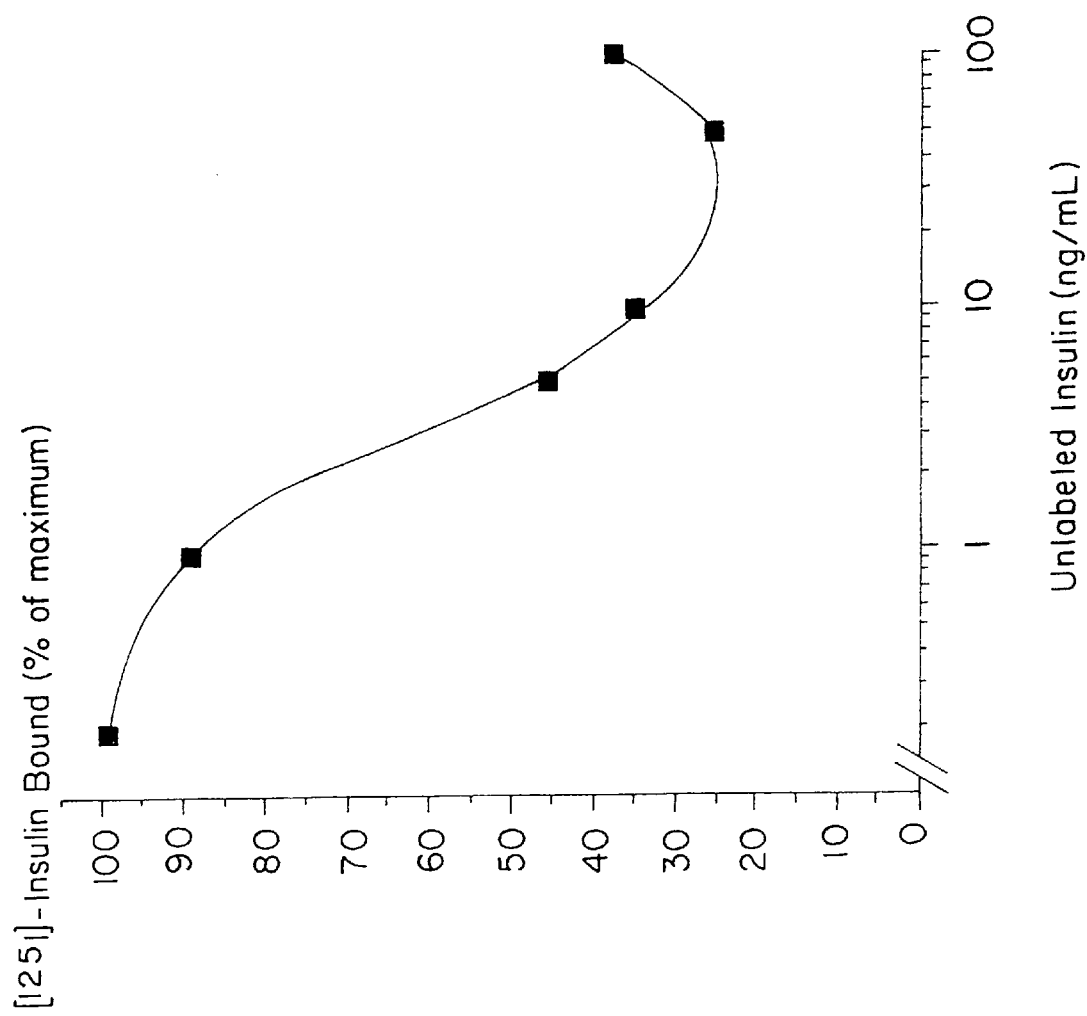
FIG. 8 shows displacement of [$^{125}$I]-insulin from the insulin receptor-like protein by unlabeled insulin.

The molecular mass of IRP corresponds to that of the mammalian holoreceptor, a disulfide-linked tetrameric glycoprotein comprised of two α and two β subunits, with masses of approximately 135 and 95 kDa, respectively. Under non-reducing conditions, the mammalian IR migrates to three discrete bands of 350, 320 and 290 kDa. The discrepancy in molecular weight between the holoreceptor and its individual subunits is a consequence of proteolysis during isolation of the more susceptible β subunit. If IRP has a subunit analogous to the α subunit of the mammalian IR, the ligand binding site should reside in a polypeptide of approximately 135 kDa. Crosslinking of purified IRP to $^{125}$I-insulin tracer, followed by reducing SDS-PAGE and autoradiography demonstrated a 135–145 kDa band (FIG. 7b). The binding was specific, as evidenced by the diminution of signal in the presence of excess insulin. [$^{125}$I]insulin was displaced from purified IRP by increasing amounts of non-radioactive hormone, with 50% of the tracer displaced by $6.6×10^{-10}$M insulin (FIG. 8). A Scatchard plot of binding displayed curvature at insulin concentrations considered supraphysiological in mammals. In yeast, as in mammals, the physiologically relevant sites are more likely to be occupied at 0.1–10 nM hormone. The high affinity binding site has a capacity for sequestering 0.67 mole of insulin/mol of receptor.

Figure 9:
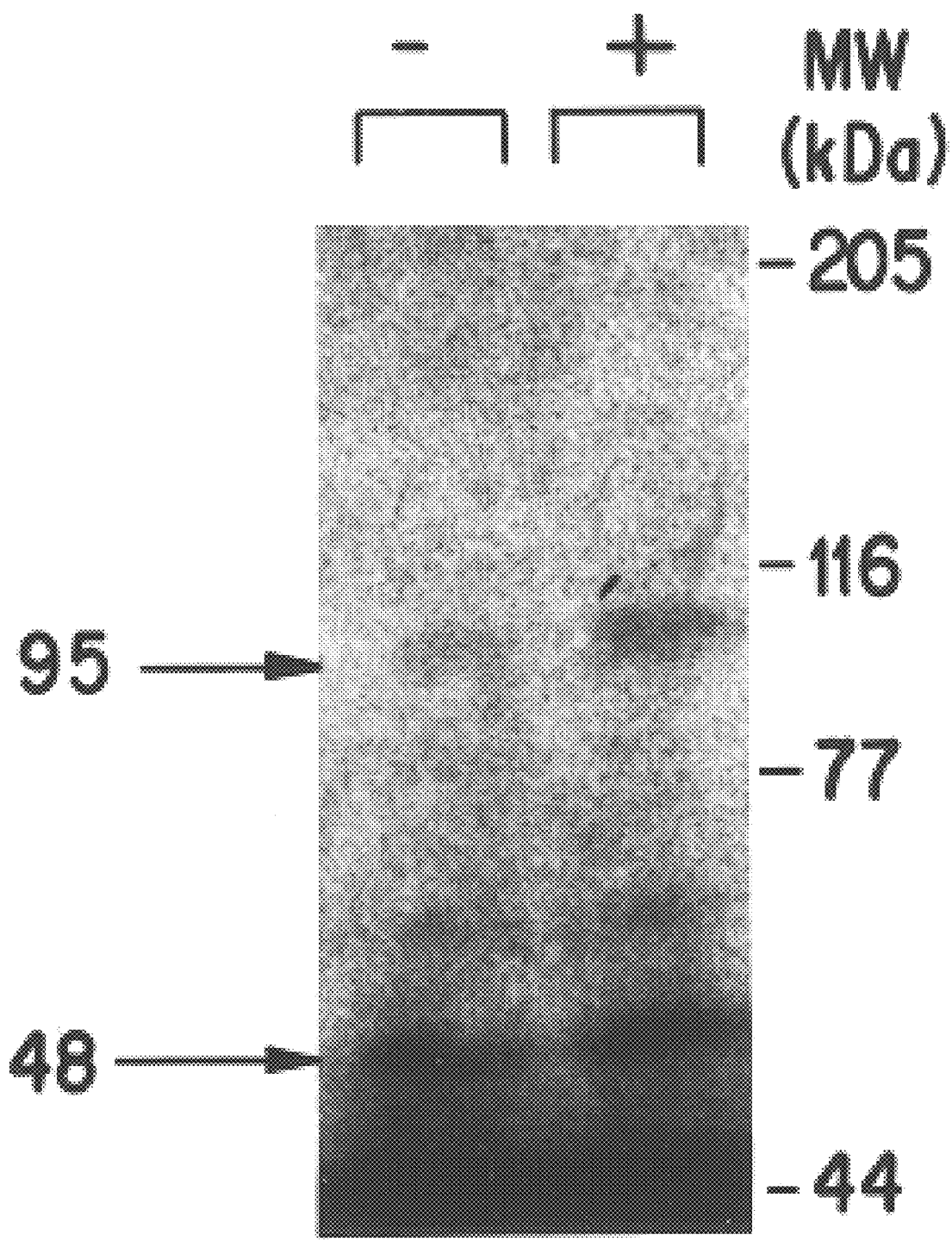
FIG. 9 shows tyrosine phosphorylated 95-kDa subunit of an insulin receptor-like protein.

The calculation of the number of binding sites was based on a molecular weight of 400 kDa and estimates of both $K_d$ and number of binding sites were not adjusted for small contributions from lower affinity receptors or cooperative interactions. The data provide a preliminary description of the high affinity site, since the data was fit to a model of single, non-interacting sites. In the presence of excess unlabeled hormone, 50% of the tracer was displaced at 0.8 nM (FIG. 9). This $K_d$ is within the physiological range of insulin binding to the IR from many responsive mammalian cell types. However, of the total binding, approximately 30% was considered nonspecific. These values are identical to those obtained from whole yeast cells and plasma membranes, and may reflect different affinities of heterologous, mammalian insulins for a widely divergent receptor from S. cerevisiae.

The yeast protein more closely resembles typical mammalian α subunits than those assigned molecular weights between 100 and 125 kDa from mammalian neuronal tissue or lower vertebrates and invertebrates. Heterogeneity of molecular weight in the α subunit probably reflects a species specific degree of glycosylation, or limited proteolysis during isolation. Therefore, the binding properties and the molecular weight are in striking agreement with all known IR α subunits.

Binding and crosslinking of [$^{125}$I]insulin were pH dependent. The species at 135–145 kDa was labeled specifically at pH 8.0, but was not evident when incubation and crosslinking was performed at lower pH. Conversely, another species at 67 kDa was visualized when incubation and crosslinking was conducted at pH 7.0, 7.5 and 8.0, but the tracer was not displaced from this moiety in the presence of excess insulin. Although specific binding was detected in solution at pH 6.5 for both species, neither was observed at that pH value because the reaction of DSS with primary amines did not reach completion during the incubation period at 4° C.

The 67 kDa protein was labeled by crosslinking to [$^{125}$I]-insulin but unlike the 135 kDa moiety, the signal was enhanced by excess unlabeled hormone (FIG. 7b). The 67 kDa polypeptide may be generated by proteolytic cleavage of the 135 kDa species, or it may be an insulin binding protein, insulin degrading enzyme or a corresponding inhibitor protein (5). A protein of similar molecular weight with IR-like binding characteristics is present in another ascomycete, N. crassa, and has been proposed to mediate metabolic and growth effects elicited by physiological concentrations of insulin in this organism.

The β subunit of the mammalian IR is a 95 kDa polypeptide with intrinsic tyrosine kinase activity. An analogous subunit in the insulin-agarose purified IRP was demonstrated by Western blotting with monoclonal antiphosphotyrosine antibodies.

Figure 10:
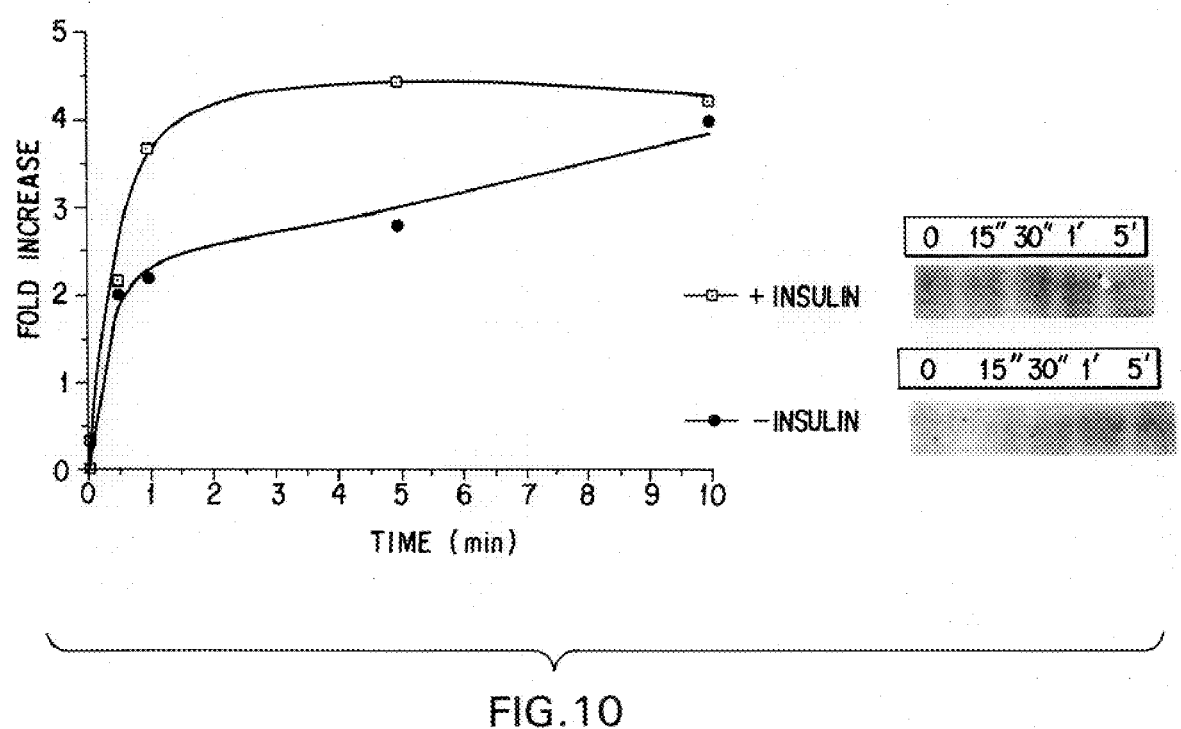
FIG. 10 shows insulin-stimulated autophosphorylation of an insulin receptor-like protein.

A low basal level of phosphorylation was detected in species of 90–95 kDa, ⁻55 kDa and in the most abundant species of 45–48 kDa (FIG. 9). When supplemented with ATP and MnCl2, strictly required cofactors for the mammalian receptor, the intensity of phosphotyrosine signals increased with time in each of the 90–95, 55, and 45–48 kDa species. (The 55 and 48 kDa species are suspected to be proteolytic fragments of the 95 kDa polypeptide.) Maximum intensity was achieved between 5–10 min, with a 3.5- to 4-fold enhancement of phosphotyrosine formation, in good agreement with previous findings (FIG. 10).

Addition of insulin increased the apparent rate of IRP autophosphorylation, and maximum signal intensity of 4-fold over the basal level was reached at 5 min, compared to 3.5-fold over the basal level gained in the absence of insulin after 10 min of incubation. IRP tyrosine kinase activity was stimulated with IGF-I and, consistent with the response to insulin, IGF-I induced rapid formation of phosphotyrosine in IRP, for a maximal stimulation of 4-fold over the basal level (FIG. 10).

Considering the low basal level of phosphotyrosine in unstimulated IRP, the magnitude of stimulation by insulin and IGF-I may indicate an upper stoichiometric boundary for phosphate incorporation into tyrosine residues, similar to the level of 5–6 phosphates per β subunit monomer documented in the mammalian receptor (23). The change in the rate of autophosphorylation is also consistent with tight coupling of kinase activity to insulin binding and an apparent increase in the $V_{max}$ of the enzyme.

The identity of the 95 kDa polypeptide as the intact kinase domain of IRP, and as the precursor of the 55 kDa and the 45–48 kDa species is supported by: 1) additivity of the molecular weight to comprise the 300–400 kDa complex observed in non-reducing gels (FIG. 7a); 2) the demonstration of tyrosine autophosphorylation by a 41 kDa cytoplasmic domain of the kinase subunit, created by systematic deletions within the mammalian IR gene to define the minimal essential region for kinase activity (17); and 3) previous reports of the smaller molecular weight moiety as the principal proteolytic product of the native 90–95 kDa subunit from mammals. Furthermore, many potential dibasic proteolytic cleavage sites distributed throughout the mammalian IR may be conserved in IRP and render it susceptible to membrane-associated KEX2 and other vacuolar proteases, to generate the observed fragments.

These studies of IRP permitted assessment of the molecular weight of the kinase and its potential for insulin-dependent signaling through tyrosine autophosphorylation, although application of traditional enzyme kinetic analyses to a protein which serves as its own substrate and has limited available sites for modification is difficult.

EXAMPLE 6

Effect of Vanadate Ion on IRP Tyrosine Phosphorylation After Insulin Binding To enhance and stabilize the phosphotyrosine signal, sodium vanadate, a general phosphatase inhibitor and insulinomimetic agent, was included in the kinase reaction mixtures. In contrast to the behavior predicted from the mammalian IR, autophosphorylation of IRP was completely inhibited by sodium vanadate (FIG. 11).

Figure 11:
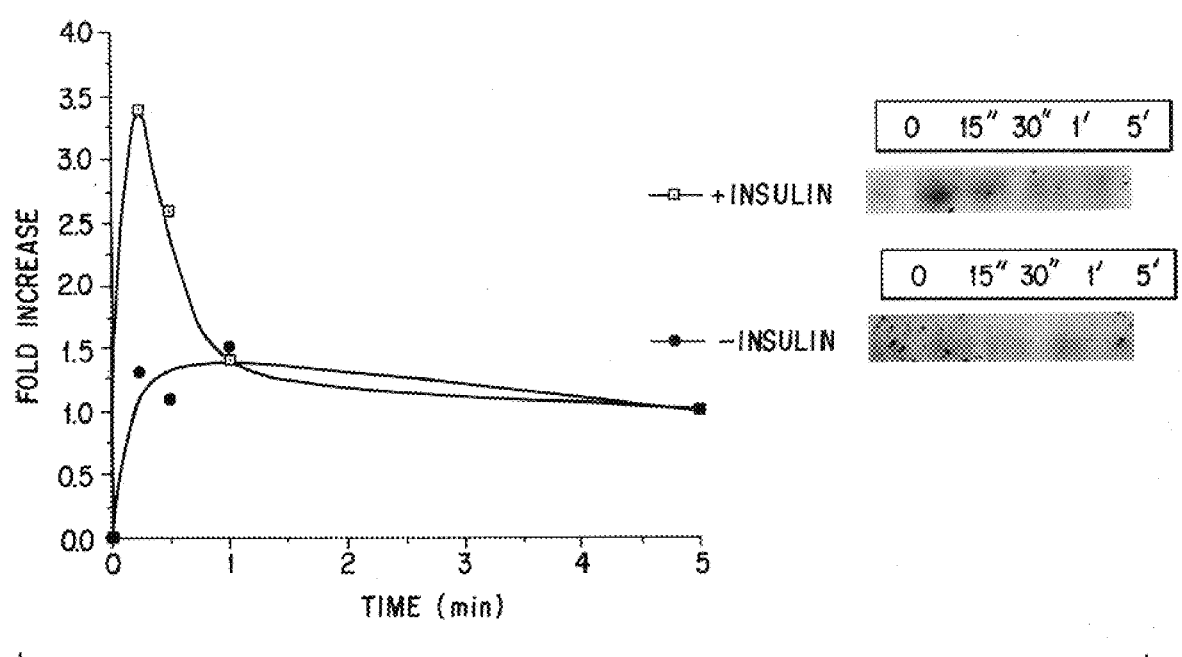
FIG. 11 shows autophosphorylation of an insulin receptor-like protein in the presence of sodium vanadate.
Figure 12:
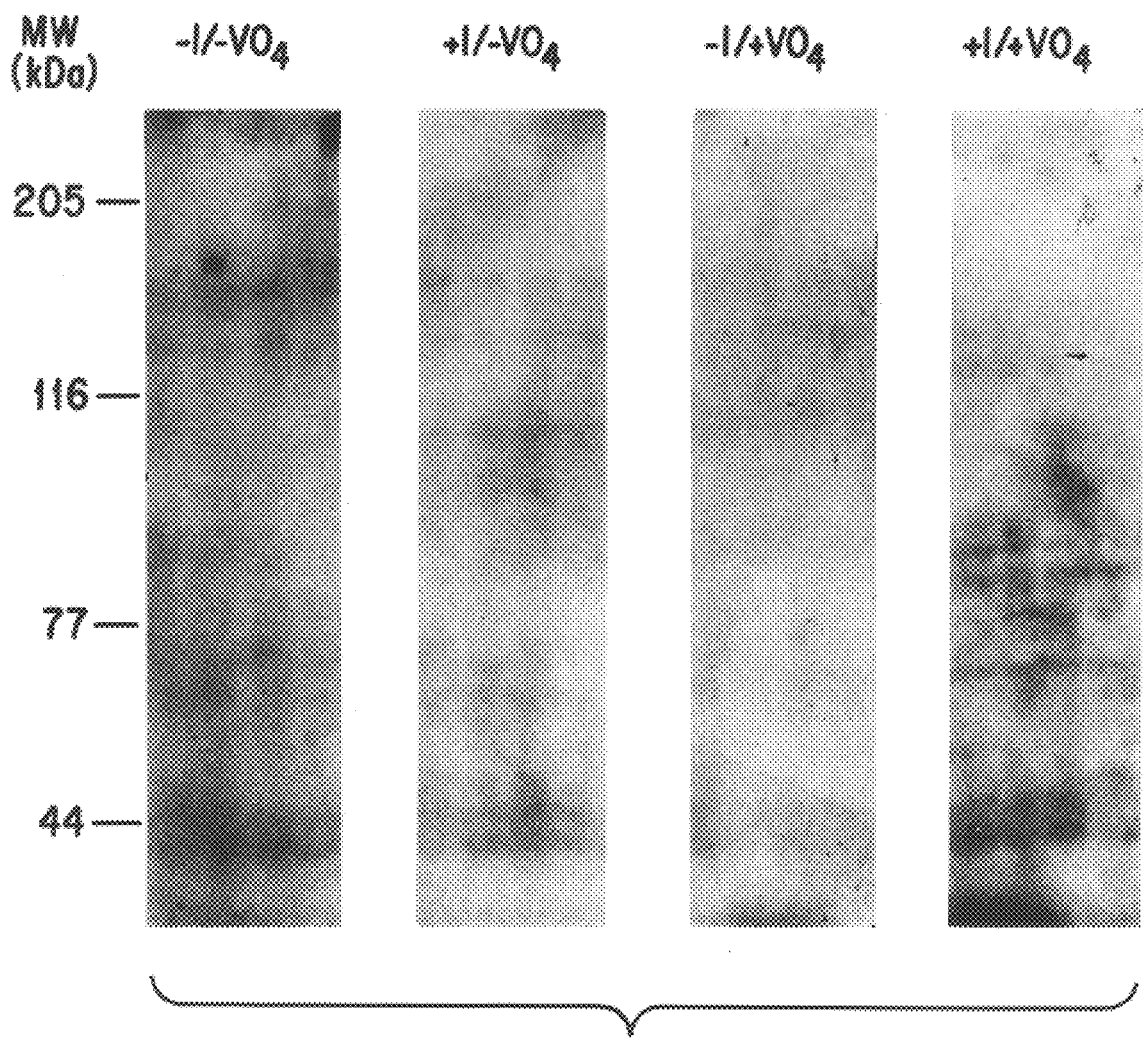
FIG. 12 shows effect of insulin and vanadate on in vivo protein in phosphorylation.

When insulin was added to the reaction mixture with sodium vanadate, the protein reached a 3.4-fold increase over the basal level of phosphotyrosine within 15 sec, but returned to the original level after 1 min (FIG. 11). This result may be explained by co-purification of a vanadate-stimulated phosphatase activity with the nearly homogeneous IRP. Exposure of intact yeast cells to insulin and sodium vanadate results in modifications of endogenous proteins that parallel the kinetics and magnitude of tyrosine phosphorylation of the isolated IRP (FIG. 12). Various phosphotyrosine-containing proteins and, notably, a 95 kDa band appear after a 10 min incubation of cells resuspended in fresh medium alone. Addition of insulin results in faster development of the 95 kDa band which can be seen after 5 min of incubation, and in a more complex pattern of phosphotyrosine-modified species. When cells were exposed to sodium vanadate, the weak signal present at 1 min of incubation was absent throughout the time course of the experiment. Concurrent exposure of cells to insulin and sodium vanadate caused intense phosphotyrosine signals in a discrete set of proteins, but the 95 kDa species was not tyrosine phosphorylated in vivo (FIG. 6).

In vitro data suggest that the kinase may have been activated by autophosphorylation prior to sample processing, but the modified substrates remained stable, even after the kinase returned to the basal state. Although the effect of sodium vanadate on the IRP-associated kinase from yeast is not known, vanadium is present in appreciable quantities in yeast cells (44 μg/g), exerts effects on lipid metabolism, synthesis of mating factors, and is required for vegetative growth in certain fungi (18).

EXAMPLE 7

Cloning a Gene Encoding the IRP From *Saccharomyces cerevisiae*

A gene encoding the IRP from *S. cerevisiae* can be cloned using a variety of approaches. *E. coil* expressing yeast proteins can be screened with antibodies that specifically bind to the IRP (see Example 10). Alternatively, nucleic acid hybridization approaches can be employed.

A genomic library is obtained from Stratagene (San Diego, Calif.). The library is made from DNA from *S. cerevisiae* strain S288c using the Lambda-DASH™ vector (catalog number 943901). The library is maintained in EPICURIAN COLI™ SURE™ bacteria, also a product of Stratagene.

Approximately $1 \times 10^7$ phage are screened using a cloned DNA fragment encoding the human insulin receptor α subunit (Oncogene Sciences, Manhasset, N.Y.). For cloning the β subunit, oligonucleotide probes can be designed by aligning the nucleotide sequences of the human, guinea pig and Drosophila insulin receptor cDNAs (GENBANK) and identifying conserved portions of the sequences. This approach is applicable to cloning of the α subunit as well.

The inserts contained within hybridizing lambda clones are completely characterized with respect to restriction map and those fragments which are found to contain DNA encoding IRP or a portion thereof are sequenced completely.

EXAMPLE 8

Expression of Cloned IRP

Yeast strains harboring disrupted null alleles of ScIRP genes can be constructed according to standard methods (20,21). Attenuated alleles can be created essentially as reported by Kataoka et al (22) for RAS genes from *S. cervisiae*. Overexpression alleles under the control of the ADH1 (alcohol dehydrogenase) or the GAL10 (galactose permease) high-copy promoters can be assembled as previously described (23–25). The gene can be overexpressed in *E. coli* (19), *Schizosaccharomyces pombe* or *S. cerevisiae*.

EXAMPLE 9

Variants of the IRP

Cloned DNA encoding the IRP can be mutated in a site-specific fashion by any of the techniques well known in the art. Most of these methods employ hybridization of one or more oligonucleotides having mismatches with the template at specific nucleotides to be mutated. Hybridization of the oligonucleotide is followed by primer extension, either as a single synthetic round to completely copy a single-stranded template or as a polymerase chain reaction. Mutants are then selected by preferential hybridization of an oligonucleotide containing the mutation and confirmed by DNA sequencing. Other mutations containing large deletions or insertions or fusions can be made by standard recombinant DNA techniques.

Variants in IRP can be expressed as described above and tested for biological activity in a number of assays. Preferably, one would assay the mutant receptors for the ability to bind to insulin-like peptides, tyrosine autophosphorylation upon ligand binding or the ability to interact with downstream effector proteins.

EXAMPLE 10

Antibodies to the IRP from S. cerevisiae

Antibodies to the IRP can be raised using any of the standard procedures known in the art. As immunogen, one can use gel-purified subunits of the IRP, identified as described above and then eluted from the gel fragment. Alternatively, successful cloning of a gene encoding each of the subunits of the IRP would allow synthesis of peptides which correspond to portions of the IRP polypeptides. The synthetic peptides are then coupled to a carrier protein, such as bovine serum albumin or keyhole limpet hemocyanin or to polystyrene beads for use in immunizing an animal, preferably a rabbit.

The invention being thus described, various modifications of the materials and methods will be apparent to one skilled in the art. Such modifications of the embodiments of the invention presented herein are to be considered within the scope of the invention as set forth in the claims below.

REFERENCES

Each of the references below is cited in the disclosure and is hereby incorporated in its entirety by such reference.

1. Broach, J. R. (1991) Ras genes in *Saccharomyces cerevisiae*: signal transduction in search of a pathway. *Trends in Genetics.*7:28–33.

2. Dailey, D., Schieven, G. L., Lim, M. Y., Marquardt, H., Gilmore, T., Thorner, J. and Martin, G. S. (1990) Novel Yeast Protein Kinase (YPK1 Gene Product) is a 40 kDa phosphotyrosyl protein associated with protein-tyrosine kinase activity. *Mol. Cell Biol.* 10:6244–6256.

3. Davis, T. N., Urder, M. S., Masiarz, F. R. and Thorner, J. (1986) Isolation of the yeast calmodulin gene: calmodulin is an essential protein. *Cell* 47:423–431.

4. Pessin, J. E., Mottola, C., Yu, K. T. and Czech, M. P. (1985) Subunit structure and regulation of the insulin-receptor complex. In *Molecular Basis of Insulin Action*. (Czech, M. P., Ed.), Plenum Press, New York, pp. 3–29.

5. Kole, H. K., Muthukumar, G. and Lenard, J. (1991) Purification and properties of a membrane-bound insulin binding protein, a putative receptor, from *Neurospora crassa*. *Biochemistry* 30:682–688.

6. White, M. F. and Kahn, C. R. (1988) Structural and functional studies of the insulin receptor kinase. In *Receptor Biochemistry and Methodology*, Vol. 12A, Insulin Receptors, Part A: Methods for the Study of Structure and Functions. Kahn, C. R. and Harrison, L. C. eds. pp. 125–145.

7. Ballou, C. E. (1982) Yeast cell wall and cell surface. In *The Molecular Biology of the Yeast Saccharomyces: Metabolism and Gene Expression*, (Strathern, J. N., Jones, E. W., and Broach, J. R., Eds.), Cold Spring Harbor Laboratories, Cold Spring Harbor, N.Y., pp. 335–360.

8. Roth, J., (1975) Assay of peptide hormones using cell receptors: Application to insulin and to human growth hormone. *Meth. Enzymol.* 37:66–81.

9. Leal-Morales, C., Bracker, C. and Bartnicki-Garcia, S. (1988) Localization of chitin synthetase in cell-free homogenates of *Saccharomyces cerevisiare*: Chitosomes and plasma membrane. *Proc. Natl. Acad. Sci. USA.* 85:8516–8520.

10. Cuatrecasas, P. (1972) *Proc. Natl. Acad. Sci. U.S.A.* 69, 1277–1281.

11. Jacobs, S., Shechter, Y., Bissell, K., and Cuatrecasas, P. (1977) *Biochem. Biophys. Res. Commun.* 77, 981–988.

12. Siegel, T. W., Ganguly, S., Jacobs, S. Rosin, O. M., and Rubin, C. S. (1981) *J. Biol. Chem.* 256, 9266–9273.

13. Fujita-Yamaguchi, Y., Choi, S., Sakamoto, Y., and Itakura, K. (1983) *J. Biol. Chem.* 258, 5045–5049

14. Lerea, K. M., and Livingston, J. N. (1988) in *Receptor Biochemistry and Methodology*, (Kahn, C. R. and Harrison, L. C., eds), Vol. 12A, pp. 205–219, Alan R. Liss, New York, N.Y.

15. Pilch, P. F. and Czech, M. P. (1980) *J. Biol. Chem.*255, 1722–1731.

16. Laemmli, U. K. (1970) *Nature* 227, 680–685

17. Kallen, R. G., Smith, J. E., Sheng, Z. and Tung, L. (1990) Expression, purification and characterization of a 41kDa insulin receptor tyrosine kinase domain. *Biochem. Biophys. Res. Commun.* 168:616–624.

18. Griffin, D. H. (1981) *Fungal Physiology*, John Wiley & Sons, New York.

19. J. Sanbrook et al, "Molecular Cloning, A Laboratory Manual", 2nd ed. 1989 by Cold Spring Harbor Laboratory Press, Cold Spring Harbor, N.Y.

20. Boguslawski, G. (1985) Yeast Transformation. In *Gene Manipualtions in Fungi*, (Bennett, J. W. and Lasure, L. L., Eds.), Academic Press, New York, pp. 161–196.

21. Botstein, D. and Davis, R. W. (1982) Principles and practice of recombinant DNA research in yeast. In *The Molecular Biology of the Yeast Saccharomyces: Metabolism and Gene Expression*, (Strathern, J. N., Jones, E. W., and Broach, J. R., Eds.), Cold Spring Harbor Laboratories, Cold Spring Harbor, N.Y., pp. 607–636.

22. Kataoka, T., Powers, S., McGill, C., Fasano, O., Strathern, J., Broach, J. and Wigler, M. (1984) Genetic analysis of yeast ras 1 and ras 2 genes. *Cell.* 37:437–445.

23. J. Rine Meth. in Enz. 194:239 (1991).

24. Broach, J., Li, Y. Y., Wu, L. C. C. and Jayaram, M. (1983) Vectors for high-level inducible expression of cloned genes in yeast. In *Experimental Manipulation of Gene Expression* (Inouye, M., Ed.), Academic Press, New York, pp. 83–177.

25. Scolnick, E., Margolis, B., Mohammadi, M., Lowenstein, E. and Schlessinger, J. (1991) Cloning of P13 kinase-associated p85 utilizing a novel method for expressing/cloning of target proteins for receptor tyrosine kinases. *Cell* 65:83–90.

I claim:

1. A method for screening a compound for insulin agonist or antagonist activity which comprises:
   i) contacting said compound with a protein of *Saccharomyces cerevisiae* that comprises:
      a first polypeptide which binds insulin and has an apparent molecular weight of 135,000 to 145,000 daltons as determined by SDS-polyacrylamide gel electrophoresis and a second polypeptide which has an apparent molecular weight of 90,000 to 95,000 daltons as determined by SDS-polyacrylamide gel electrophoresis and is phosphorylated on tyrosine in response to binding of insulin by said first polypeptide, wherein
      said first and second polypeptides associate to form an $\alpha_2\beta_2$ heterotetramer;
      said first and second polypeptides are joined by at least one disulfide linkage;
      said first polypeptide is glycosylated;
      said protein requires a divalent metal ion for said phosphorylation of tyrosine in response to binding of insulin;
      said protein binds human insulin with a $K_d$ of about $8 \times 10^{-10}$ M and binds human insulin-like growth factor 1 with a $K_d$ of about $4 \times 10^{-10}$ M; and
   ii) determining if the contacting of said compound with said protein alters binding of insulin to said protein.

2. A method for screening a compound for insulin agonist or antagonist activity which comprises:
   i) contacting said compound with a protein of *Saccharomyces cerevisiae* that comprises
      a first polypeptide which binds insulin and has an apparent molecular weight of 135,000 to 145,000 daltons as determined by SDS-polyacrylamide gel electrophoresis and a second polypeptide which has an apparent molecular weight of 90,000 to 95,000 daltons as determined by SDS-polyacrylamide gel electrophoresis and is phosphorylated on tyrosine in response to binding of insulin by said first polypeptide, wherein
      said first and second polypeptides associate to form an $\alpha_2\beta_2$ heterotetramer;
      said first and second polypeptides are joined by at least one disulfide linkage;
      said first polypeptide is glycosylated;
      said protein requires a divalent metal ion for said phosphorylation of tyrosine in response to binding of insulin;
      said protein binds human insulin with a $K_d$ of about $8 \times 10^{-10}$ M and binds human insulin-like growth factor 1 with a $K_d$ of about $4 \times 10^{-10}$ M;
   ii) contacting said bound insulin with said compound to be screened for insulin agonist or antagonist activity; and
   iii) measuring the amount of bound insulin displaced by said compound to be screened for insulin agonist or antagonist activity.

3. A method for screening a compound for activity as an activator or inhibitor of autophosphorylation of insulin receptor, which comprises:
   i) contacting said compound, in the presence of a divalent metal ion, with a protein of *Saccharomyces cerevisiae* that comprises:
      a first polypeptide which binds insulin and has an apparent molecular weight of 135,000 to 145,000 daltons as determined by SDS-polyacrylamide gel electrophoresis and a second polypeptide which has an apparent molecular weight of 90,000 to 95,000 daltons as determined by SDS-polyacrylamide gel electrophoresis and is phosphorylated on tyrosine in response to binding of insulin by said first polypeptide, wherein
      said first and second polypeptides associate to form an $\alpha_2\beta_2$ heterotetramer;
      said first and second polypeptides are joined by at least one disulfide linkage;
      said first polypeptide is glycosylated;
      said protein requires a divalent metal ion for said phosphorylation of tyrosine in response to binding of insulin;
      said protein binds human insulin with a $K_d$ of about $8 \times 10^{-10}$ M and binds human insulin-like growth factor 1 with a $K_d$ of about $4 \times 10^{-10}$ M; and
   ii) measuring the amount of phosphotyrosine in a protein selected from the group consisting of said second polypeptide, a protein of about 135,000 daltons molecular weight, a protein of about 112,000 daltons molecular weight, a protein of about 87,000 daltons molecular weight, a protein of about 81,000 daltons molecular weight, a protein of about 74,000 daltons molecular weight, a protein of about 65,000 daltons molecular weight, a protein of about 46,000 daltons molecular weight and a protein of about 44,000 daltons molecular weight.

4. The method of claim 3, which further comprises contacting said protein with insulin prior to performing step (ii).

5. The method of claim 1, wherein said protein of *Saccharomiyces cerevisiae* is present as a crude membrane preparation.

6. The method of claim 1, wherein said protein of *Saccharomyces cerevisiae* is substantially purified.

7. The method of claim 2, wherein said protein of *Saccharomyces cerevisiae* is present as a crude membrane preparation.

8. The method of claim 2, wherein said protein of *Saccharomyces cerevisiae* is substantially purified.

9. The method of claim 3, wherein said protein of *Saccharomyces cerevisiae* is present as a crude membrane preparation.

10. The method of claim 3, wherein said protein of *Saccharomyces cerevisiae* is substantially purified.

11. The method of claim 4, wherein said protein of *Saccharomyces cerevisiae* is present as a crude membrane preparation.

12. The method of claim 4, wherein said protein of *Saccharomyces cerevisiae* is substantially purified.

13. The method of claim 3, wherein the amount of phosphotyrosine is measured in said second polypeptide.

14. The method of claim 4, wherein the amount of phosphotyrosine is measured in said second polypeptide.

15. The method of claim 9, wherein the amount of phosphotyrosine is measured in said second polypeptide.

16. The method of claim 10, wherein the amount of phosphotyrosine is measured in said second polypeptide.

17. The method of claim 11, wherein the amount of phosphotyrosine is measured in said second polypeptide.

18. The method of claim 12, wherein the amount of phosphotyrosine is measured in said second polypeptide.

19. A method for screening a compound for insulin agonist or antagonist activity which comprises:
   i) contacting said compound with a protein of *Saccharomyces cerevisiae* that comprises:

a first polypeptide which binds insulin and has an apparent molecular weight of 135,000 to 145,000 daltons as determined by SDS-polyacrylamide gel electrophoresis and a second polypeptide which has an apparent molecular weight of 90,000 to 95,000 daltons as determined by SDS-polyacrylamide gel electrophoresis and is phosphorylated on tyrosine in response to binding of insulin by said first polypeptide, wherein said first and second polypeptides associate to form an $\alpha_2\beta_2$ heterotetramer;

said first and second polypeptides are joined by at least one disulfide linkage;

said first polypeptide is glycosylated;

said protein requires a divalent metal ion for said phosphorylation of tyrosine in response to binding of insulin;

said protein binds human insulin with a $K_d$ of about $8 \times 10^{-10}$ M and binds human insulin-like growth factor 1 with a $K_d$ of about $4 \times 10^{-10}$ M; and ii) determining if the contacting of said compound with said protein alters the biochemical activity of a downstream effector of the insulin signaling pathway.

* * * * *